US00PP33142P2

(12) United States Plant Patent
Ranney et al.

(10) Patent No.: US PP33,142 P2
(45) Date of Patent: Jun. 8, 2021

(54) ***HYDRANGEA* PLANT NAMED 'NCHA6'**

(50) Latin Name: *Hydrangea arborescens*
Varietal Denomination: NCHA6

(71) Applicant: North Carolina State University, Raleigh, NC (US)

(72) Inventors: Thomas Green Ranney, Arden, NC (US); Darren H. Touchell, Raleigh, NC (US); Irene Palmer, Raleigh, NC (US); Andra Windorf Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/902,703

(22) Filed: Jun. 16, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

(56) References Cited

PUBLICATIONS

UPOV hit on *Hydreangea* plant named, 'NCHA6', CAPBR 20-10252, filed May 22, 2020.*

* cited by examiner

*Primary Examiner* — Anne Marie Grunberg
(74) *Attorney, Agent, or Firm* — Cassandra Bright

(57) ABSTRACT

A new and distinct cultivar of *Hydrangea* plant named 'NCHA6' is disclosed, characterized by a compact habit and large, mop-head inflorescences with dark red-purple sepals. 'NCHA6' is a triploid cultivar with extended reblooming that often continues into the fall. The new variety is a *Hydrangea*, normally produced as an outdoor garden or container plant.

3 Drawing Sheets

Figure 1:
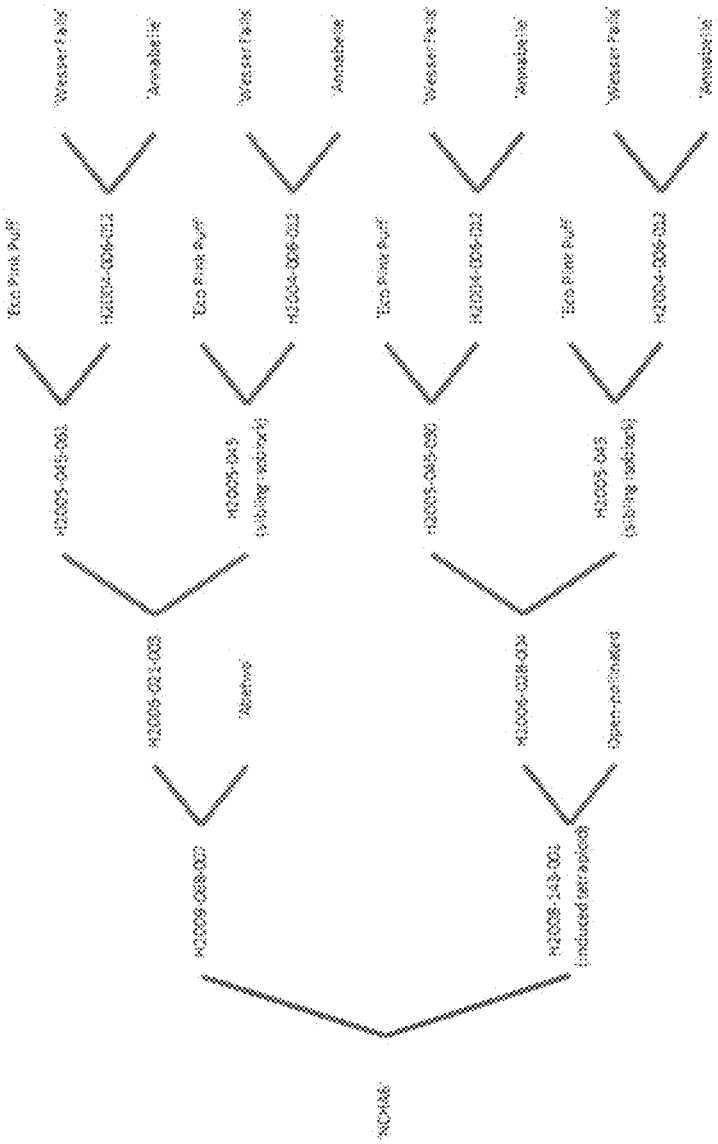

Latin name of the genus and species: *Hydrangea arborescens*.

Variety denomination: 'NCHA6'.

BACKGROUND OF THE INVENTION

The new *Hydrangea* cultivar is a product of a planned breeding program conducted by the inventor in Mills River, N.C. The cross resulting in this new variety was made during Summer of 2011. The objective of the breeding program was to develop new forms and flower colors of *Hydrangea arborescens* for commercial horticultural purposes.

The seed parent of 'NCHA6' is the unpatented, proprietary seedling referred to as 'H2009-068-007'. The pollen parent is the unpatented, proprietary seedling referred to as 'H2008-143-001'. The new variety was identified as a potentially interesting selection in the Spring of 2012, at a research greenhouse in Mills River, N.C.

The first asexual propagation of 'NCHA6' was carried out in Spring of 2012 by softwood cuttings at the same research greenhouse in Mills River, N.C. and has been asexually reproduced repeatedly. 'NCHA6' has been found to retain its distinctive characteristics through successive asexual propagations.

SUMMARY OF THE INVENTION

The cultivar 'NCHA6' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCHA6' These characteristics in combination distinguish 'NCHA6' as a new and distinct *Hydrangea* cultivar:

1. Large mop-head flowers.
2. Dark red-purple sepals.
3. Compact plants.
4. Extended reblooming.
5. Triploid.

PARENT COMPARISON

Plants of the new cultivar 'NCHA6' are similar to plants of the seed parent in most horticultural characteristics, however, plants of the new cultivar 'NCHA6' differ in the following;

1. The new variety has darker red-purple sterile sepals.
2. The new variety is a triploid, the seed parent is diploid.

Plants of the new cultivar 'NCHA6' are similar to plants of the pollen parent in most horticultural characteristics, however, plants of the new cultivar 'NCHA6' differ in the following;

1. The new variety has darker red-purple sterile sepals.
2. The new variety is a triploid, the pollen parent is tetraploid.

COMMERCIAL COMPARISON

Plants of the new cultivar 'NCHA6' can be compared to the commercial variety *Hydrangea* 'NCHA7' U.S. Plant Pat. No. 30,358. These varieties are similar in most horticultural characteristics; however, 'NCHA6' differs in the following:

1. 'NCHA6' begins blooming later.
2. Sterile sepal color of the new variety is a different shade of red-purple.

BRIEF DESCRIPTION OF THE PHOTOGRAPHS

This new smooth-leaf *Hydrangea* (*Hydrangea arborescens*) is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Hydrangea* cultivar.

FIG. 1. Pedigree of *Hydrangea arborescens* 'NCHA6'.

Figure 2:
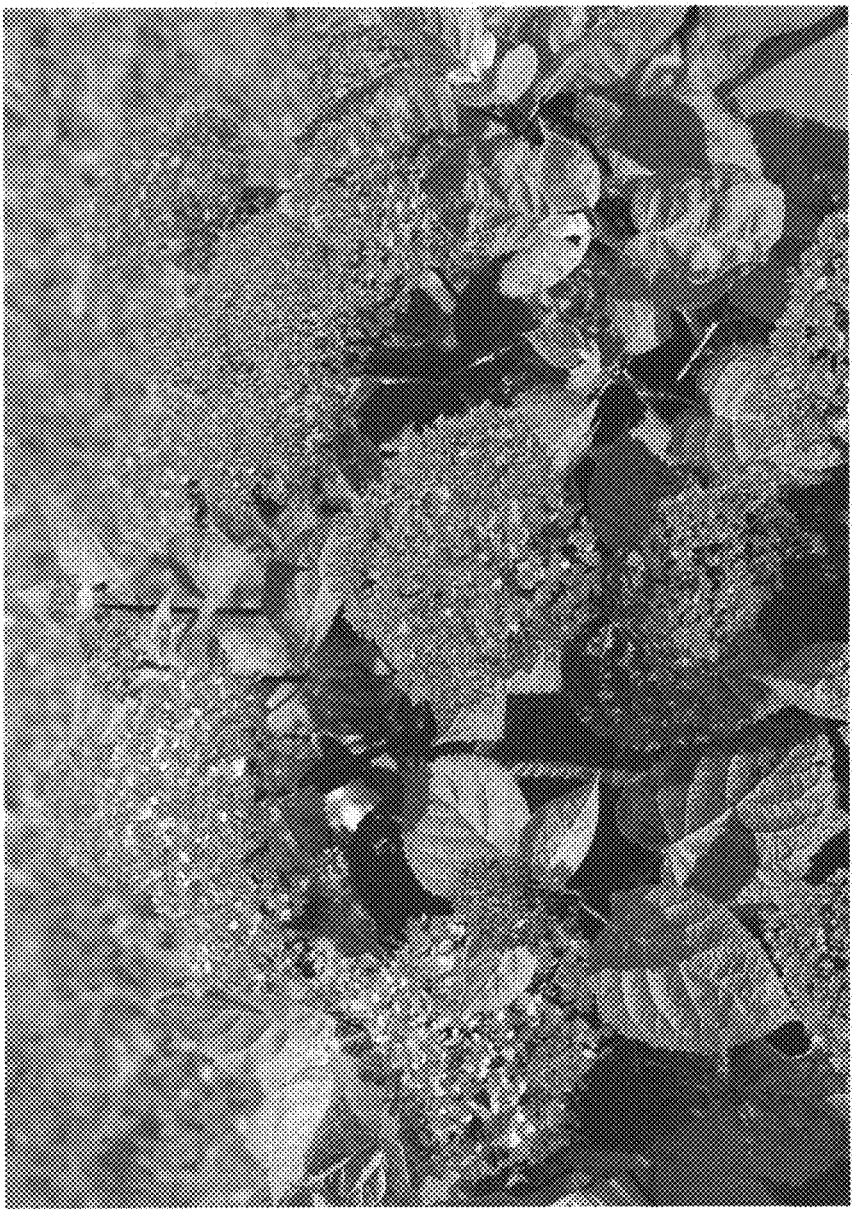

FIG. 2 Shows new flowers emerging on 'NCHA6' as well as its habit. Photo is of a 3-year old plant in container trials located in Grand Haven, Mich.

Figure 3:
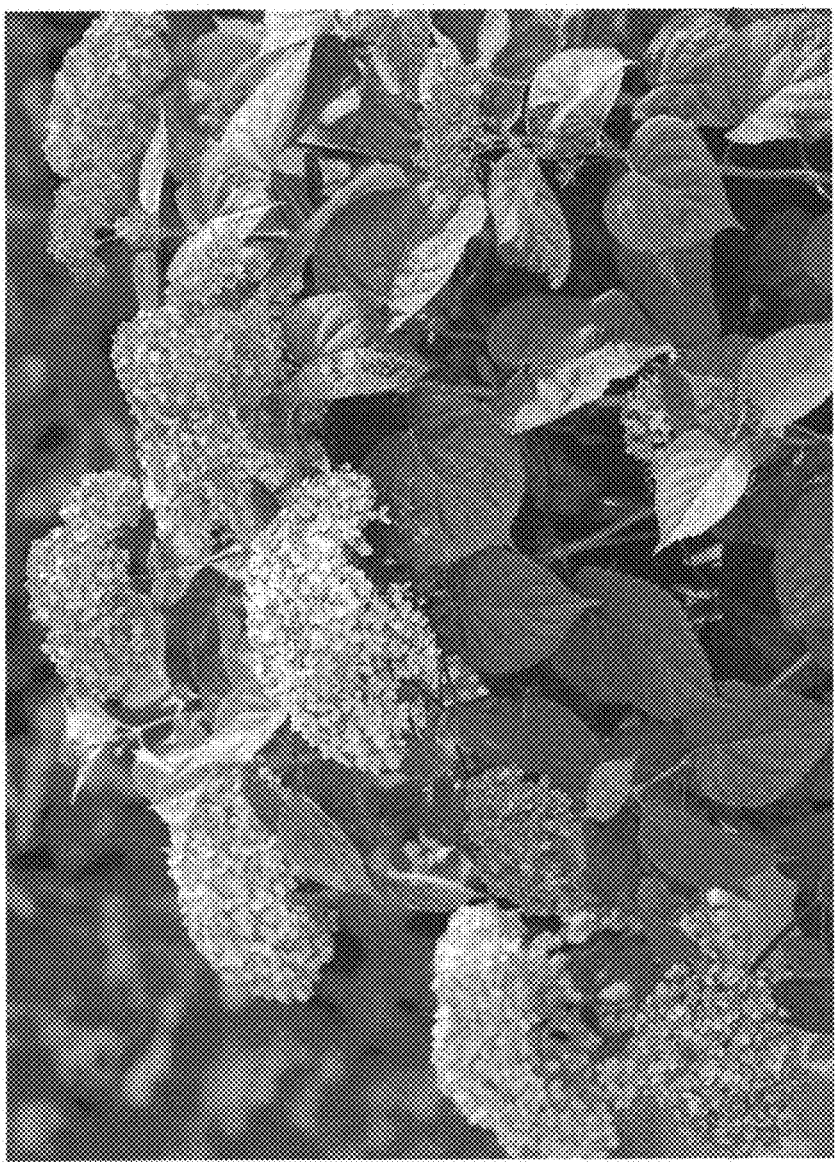

FIG. 3: Shows the progression of flowering in a 3-year old container plant growing in Grand Haven, Mich.

DETAILED BOTANICAL DESCRIPTION

The following is a detailed description of the botanical characteristics of the new and distinct smooth *Hydrangea* (*Hydrangea arborescens*) known by the denomination 'NCHA6'. The detailed description was taken on a 3-year-old container-grown plant in Mills River, N.C. in 2019. All colors cited herein refer to The Royal Horticultural Society Colour Chart (The Royal Horticultural Society (R.H.S.), London, 2001 Edition). Where pertinent, descriptive data was supplemented with information provided from cooperators in Grand Haven, Mich. where data was taken on 3-year-old container plants as well as plants in a landscape setting. Where specific dimensions, sizes, colors, and other characteristics are given, it is to be understood that such characteristics are approximations or averages set forth as accurately as practicable.

Botanical classification: *Hydrangea arborescens* 'NCHA6'.

PROPAGATION

Time to initiate roots: About 20 days at approximately 18 to 27° C.

Root description: Density is moderate to dense, fibrous, freely branching. Mature root is colored Yellow 9B.

Time to produce a rooted young plant: About 90 days.

PLANT

Plant type: Perennial deciduous flowering shrub.

Growth habit: Compact, rounded.

Overall plant shape: Upright/rounded.

Height: 70 to 80 cm.

Plant spread: 80 to 90 cm.

Shoot and stem:

*Length*.—Variable, approximately 20-60 cm.

*Diameter*.—Approximately 2-6 mm.

*Internode length*.—Average length is 5 cm, ranging from 1-7 cm.

*Immature shoot texture* (*current year*).—Slightly pubescent.

*Immature shoot color* (*current year*).—RHS Yellow-Green Group 144B.

*Mature stem texture* (*growth from the previous year*).—Woody, exfoliating.

*Mature stem color* (*growth from the previous year*).—Mix of RHS Yellow-Green Group N148A with exfoliating epidermis which is a mix of RHS Greyed-Green Group 197A and RHS Grey-Brown Group 199B through 199C.

FOLIAGE

Leaf:

Type: Simple.

*Persistence*.—Deciduous.

*Arrangement*.—Opposite

*Shape*.—Ovate.

*Apex*.—Acuminate.

*Base*.—Rounded, obtuse.

*Venation*.—Reticulate.

*Vein color*.—Abaxial (upper): RHS Yellow-Green Group 146D. Adaxial (lower): RHS Yellow-Green Group 146D.

*Margins*.—Serrate.

*Emerging leaves*.—Color: Abaxial (upper): Mix of RHS Yellow-Green Group 144A and RHS Yellow-Green Group 146B. Adaxial (lower): RHS Yellow-Green Group 146B. Texture: Lightly pubescent on both leaf sides.

*Mature leaves* (*from the current season*).—Color: Abaxial (upper): Mix of RHS Green Group 139A and RHS Greyed-Green Group N189A. Adaxial (lower): RHS Green Group NN137D. Texture: Lightly pubescent on both leaf sides. Length of lamina: Ranges from 5-10 cm, average is approximately 8 cm. Width of lamina: Ranges from 3-7 cm, average is approximately 6 cm.

*Leaf attachment*.—Petiolate.

*Petiole*.—Length: Ranges from 2-8 cm. Diameter: Ranges from 1-3 mm. Color: RHS Yellow-Green Group 146D. Texture: Lightly pubescent.

FLOWER

Description: Inflorescence is a compound corymb composed of fertile and sterile flowers arranged in a hemispherical or dome-shaped terminal inflorescence. Corymbs are globular in shape. Individual corymbs range in diameter from approximately 9-20 cm, averaging approximately 15 cm. They range in height from 5-12 cm, averaging approximately 7 cm. There are approximately 35-60 corymbs produced each season per plant. Each corymb contains between approximately 150 to over 1000 sterile flowers and approximately 100-600 fertile flowers. Average is approximately 400 sterile and 200 fertile flowers.

*Flowering season*.—Early summer (late June-Early July) into the fall (blooms observed into late October in Mills River, N.C.).

Sterile flowers: Single flowers with highly reduced/inconspicuous androecia/gynoecia (<0.5 mm).

*Buds*.—Shape: Ovate. Diameter: Approximately 1-3 mm. Color: RHS Yellow-Green Group 145C-D.

*Sepals*.—Number: Generally 4, ranging from 2-5. Length: Approximately 1 cm, ranging from 0.5-1.5 cm. Width: Approximately 1 cm, ranging from 0.5-1 cm. Shape: Ovate. Apex: Broadly acute, often rounded. Base: Rounded. Margin: Entire. Texture: Smooth, silky. Color: Emerging flowers — Adaxial (upper): RHS Green-White Group 157A mixed with RHS Red-Purple Group 60A-C along the edge. Abaxial (lower): RHS Red-Purple Group 60A-C. At Anthesis — Adaxial (upper): RHS Orange-White Group 159C mixed with RHS Red-Purple Group 64B. Abaxial (lower): RHS Red-Purple Group 65C mixed with RHS Red-Purple Group 67C. Post Anthesis — Adaxial (upper): RHS Yellow-Green Group N144D-145B-C. Some blushing around the edge. Abaxial (lower): RHS Yellow-Green Group 145A-C mixed with RHS Red-Purple Group 68B-C.

Fertile flowers: Sepals and petals are highly reduced (<0.5 mm).

*Buds*.—Shape: Rounded. Diameter: Approximately 1.5-2.5 mm. Color: RHS White Group 155A.

REPRODUCTIVE ORGANS

Gynoecium:

*Pistil number*.—2.

*Pistil color*.—RHS White Group NN155D.

*Pistil length*.—Approximately 1 mm.

*Stigma shape*.—Blunt.

*Stigma diameter*.—Approximately 0.5 mm.

*Stigma color*.—RHS White Group NN155D.

*Style length*.—Highly reduced, less than 0.5 mm.

*Ovary shape*.—Rounded.

*Ovary diameter*.—Approximately 1.5-2 mm.

Androecium:

*Stamen number*.—10.

*Filament length*.—0.5-1 mm.

*Filament color*.—RHS White Group NN155A.

*Anther shape*.—Rounded, having two chambers.

*Anther length*.—Approximately 0.8 mm.

*Anther color*.—RHS White Group NN155A.

*Amount/color of pollen*.—Present but reduced.

OTHER CHARACTERISTICS

Fruit type: Capsule. Seed is minute, dust-like, and rare.

Disease and insect resistance: No significant resistance nor susceptibility to disease or insect pests has been observed.

Cold hardiness: Cold hardy to at least USDA zone 6b, testing has not been completed in colder zones.

What is claimed is:

1. A new and distinct cultivar of *Hydrangea* plant named 'NCHA6' as herein illustrated and described.

* * * * *